United States Patent
Brodeur

(10) Patent No.: US 8,088,158 B2
(45) Date of Patent: Jan. 3, 2012

(54) RADIOPAQUE EPTFE MEDICAL DEVICES

(75) Inventor: Christopher Brian Brodeur, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/324,367

(22) Filed: Dec. 20, 2002

(65) Prior Publication Data

US 2004/0122509 A1    Jun. 24, 2004

(51) Int. Cl.
*A61F 2/06*    (2006.01)
(52) U.S. Cl. ............ 623/1.34; 623/1.13; 623/1.49
(58) Field of Classification Search ......... 623/1.1, 623/11.11, 12, 1.13, 1.34, 1.45, 1.49–1.54; 606/191–198; 600/36
See application file for complete search history.

(56) References Cited

U.S. PATENT DOCUMENTS

| | | | |
|---|---|---|---|
| 3,368,944 A * | 2/1968 | Sandmark et al. | 424/9.411 |
| 3,953,566 A | 4/1976 | Gore | |
| 3,962,153 A | 6/1976 | Gore | |
| 4,254,180 A * | 3/1981 | Kline | 428/323 |
| 4,973,609 A | 11/1990 | Browne | |
| 4,985,296 A * | 1/1991 | Mortimer, Jr. | 428/220 |
| 4,990,138 A | 2/1991 | Bacich et al. | 604/96 |
| 5,024,232 A * | 6/1991 | Smid et al. | 600/431 |
| 5,148,806 A * | 9/1992 | Fukui et al. | 600/341 |
| 5,201,314 A * | 4/1993 | Bosley et al. | 600/458 |
| 5,269,810 A * | 12/1993 | Hull et al. | 607/129 |
| 5,319,059 A | 6/1994 | Neuenschwander et al. | 528/73 |
| 5,320,100 A * | 6/1994 | Herweck et al. | 600/431 |
| 5,462,781 A | 10/1995 | Zukowski | |
| 5,464,438 A * | 11/1995 | Menaker | 623/1.43 |
| 5,476,589 A | 12/1995 | Bacino | |
| 5,665,114 A * | 9/1997 | Weadock et al. | 623/1.34 |
| 5,667,523 A * | 9/1997 | Bynon et al. | 623/1.13 |
| 5,700,285 A * | 12/1997 | Myers et al. | 623/1.13 |
| 5,735,892 A * | 4/1998 | Myers et al. | 623/1.13 |
| 5,810,870 A * | 9/1998 | Myers et al. | 623/1.13 |
| 5,817,017 A * | 10/1998 | Young et al. | 600/433 |
| 5,843,171 A * | 12/1998 | Campbell et al. | 606/198 |
| 5,925,075 A * | 7/1999 | Myers et al. | 623/1.13 |
| 5,993,489 A * | 11/1999 | Lewis et al. | 623/1.13 |
| 6,001,125 A * | 12/1999 | Golds et al. | 623/23.7 |
| 6,004,348 A * | 12/1999 | Banas et al. | 623/23.7 |
| 6,019,787 A | 2/2000 | Richard et al. | 623/1 |
| 6,048,362 A | 4/2000 | Berg | 623/1.34 |

(Continued)

FOREIGN PATENT DOCUMENTS

EP     0 203 833 B1    11/1988

(Continued)

OTHER PUBLICATIONS

International Search Report issued in International Application No. PCT/US03/26514 filed Aug. 26, 2003.

(Continued)

*Primary Examiner* — David Isabelle
*Assistant Examiner* — Andrew Iwamaye
(74) *Attorney, Agent, or Firm* — Vidas, Arrett & Steinkraus, P.A.

(57) ABSTRACT

A radiopaque implantable prosthesis including a polymeric prosthesis made from ePTFE having a node and fibril structure and a radiopaque filler integral with at least a portion of the node and fibril structure of the ePTFE. A method of making the prosthesis is also provided.

9 Claims, 3 Drawing Sheets

U.S. PATENT DOCUMENTS

| | | | | |
|---|---|---|---|---|
| 6,120,532 | A | 9/2000 | Goldfarb | 623/1 |
| 6,174,330 | B1 * | 1/2001 | Stinson | 623/1.34 |
| 6,200,338 | B1 * | 3/2001 | Solomon et al. | 623/1.34 |
| 6,203,735 | B1 * | 3/2001 | Edwin et al. | 264/127 |
| 6,253,769 | B1 | 7/2001 | LaFontaine et al. | 128/898 |
| 6,296,661 | B1 * | 10/2001 | Davila et al. | 623/1.13 |
| 6,379,381 | B1 * | 4/2002 | Hossainy et al. | 623/1.42 |
| 6,660,301 | B1 * | 12/2003 | Vogel et al. | 424/489 |
| 6,673,102 | B1 * | 1/2004 | Vonesh et al. | 623/1.13 |
| 6,726,696 | B1 * | 4/2004 | Houser et al. | 606/151 |
| 6,758,858 | B2 * | 7/2004 | McCrea et al. | 623/1.13 |
| 2001/0023370 | A1 * | 9/2001 | Smith et al. | 623/1.13 |
| 2001/0025131 | A1 * | 9/2001 | Edwin et al. | 600/36 |
| 2002/0095205 | A1 * | 7/2002 | Edwin et al. | 623/1.13 |
| 2002/0103528 | A1 * | 8/2002 | Schaldach et al. | 623/1.15 |
| 2002/0198588 | A1 * | 12/2002 | Armstrong et al. | 623/1.13 |
| 2003/0004563 | A1 * | 1/2003 | Jackson et al. | 623/1.15 |

FOREIGN PATENT DOCUMENTS

| | | | |
|---|---|---|---|
| GB | 2182566 A | * | 5/1987 |
| JP | H02-123240 | | 10/1990 |
| JP | 2002-501779 | | 1/2002 |
| JP | 2002-540854 | | 12/2002 |
| WO | WO 90/03036 | | 3/1990 |
| WO | WO 9703812 A | * | 2/1997 |
| WO | WO 01/49340 A1 | | 7/2001 |
| WO | WO 0158504 A1 | * | 8/2001 |
| WO | 0241804 | | 5/2002 |

OTHER PUBLICATIONS

Extract from Oxford Medical Dictionary, 2002, 4 pages.

* cited by examiner

RADIOPAQUE EPTFE MEDICAL DEVICES

FIELD OF THE INVENTION

The present invention relates to radiopaque polymeric medical devices. More particularly, the present invention relates to biocompatible and biostable medical devices made from a biocompatible polymer such as expanded or stretched polytetrafluoroethylene (PTFE) which incorporates a radiopaque material therein.

BACKGROUND OF THE INVENTION

The use of implantable medical devices such as grafts, stents, and the like, has increased steadily since these devices were first developed. Stents or grafts are usually implanted into a variety of body vessels or lumens in an effort to maintain their patency and are particularly useful, for example, in the treatment of vascular diseases such as atherosclerotic stenosis or aneurysms in blood vessels.

In order for implantable medical devices to successfully perform their function, they must be biocompatible. In particular, it is important for a graft to be porous so as to allow cell ingrowth so that the graft becomes an integrated part of the body lumen. The graft must also be biologically inert so as to avoid excessive tissue growth, scarring, and blocking of the graft. A particularly advantageous compound for forming the graft is PTFE. This polymer is biocompatible as it is biologically inert and can be formed into appropriately sized lumens or tubes to meet various arterial and vascular needs. Furthermore, the method of making PTFE tubes, especially expanded PTFE (ePTFE) tubes, produces a desirable porosity. This feature encourages incorporation of the graft material into the body lumen while avoiding excessive cell growth, scarring, and blockage. However, use of PTFE in making grafts results in a product that is not radiopaque.

For a number of reasons, it is important to be able to see the implanted medical device using fluoroscopic methods. Fluoroscopy is useful in facilitating the precise placement during implantation of medical devices such as grafts or stents. After initial placement, fluoroscopy is useful in monitoring the status of the structure. Characteristics of a flexible graft that may be monitored using fluoroscopy include location of the graft, compliance of the graft, the anastomosis of the graft to the patient's body organ tubing, and the presence or absence of conditions such as holes, kink failures, bursts, aneurysm, and the like.

To date, a number of methods and devices have been developed that impart radiopacity to medical devices and/or implantation devices in order to satisfy these needs. For implantation of medical devices, a variety of radiopaque guide wires have been developed. The guide wire is usually inserted into the medical device and this assembly is guided through and inserted into a lumen of the body. The wire is usually made of an inherently radiopaque material. Placement of the medical device is tracked by fluoroscopically observing the wire as it guides the medical device into place. The disadvantage of this method is that once the medical device is in place, the radiopaque wire is removed. As a result, the implanted medical device remains invisible to fluoroscopic analysis after implantation.

One method of rendering medical devices detectable by fluoroscopy is the use of radiopaque metal markers placed directly on the medical device either at the ends or along the length of the device. See, for example, U.S. Pat. No. 6,253,769. These markers are of limited use in fluoroscopic detection of the flexible graft characteristics detailed above. Since only a portion of the graft is visible, holes and the like will go undetected. Furthermore, these markers are not particularly useful in implantable devices that are required to be porous and flexible, such as vascular prosthesis. Vascular grafts, including those which are surgically implanted and those which are introduced intraluminally, are designed to mimic the natural vessels and hence require a unique combination of features to be present. The graft must be sufficiently porous to allow formation of the altima, and encapsulation by the body, yet be fluid-tight to prevent leakage of blood. Additionally, flexibility and compliance are also key features of a successful graft product. Thus, use of metal bands or conventional radiopaque markers are unacceptable in such devices.

Fluoroscopically visible medical devices are known which use radiopaque polymers. Larsen, European Patent Publication No. 0 203 833, discloses a composition comprising a x-ray contrasting thermoset polymer including a crosslinkable polyester resin dissolved in a vinyl monomer. This composition may be used to manufacture surgical articles. However, due to the solid polymer's inflexibility, it may not be used to create flexible devices and would certainly be inappropriate to use as any type of prosthetic implant which requires flexibility.

U.S. Pat. No. 5,319,059 to Neuenschwander et al. discloses a biocompatible radiopaque material covalently attached to a polyurethane matrix. However, many polyurethane materials are known to be inherently unstable in the body over time, and may be reabsorbed into the body, rendering the article invisible by radiographic imaging. This may be problematic for applications to implantable articles, whose presence would become undetectable to X-rays after decomposition of the radiopaque material.

WO 90/03036 published application discloses use of polymer compositions having added inorganic heavy metal salts in a physical mixture for use in medical and dental applications. The heavy metal is present as a fine powder locked in a matrix. However, preparation of these compositions may result in an uneven distribution of salt which has an adverse effect on the plasticity of the composition. Furthermore, the salts tend to gradually leach out of such matrices releasing toxic heavy metals into the system. Composite polymers are also known but these are only possible with polymers having appropriate reaction sites, such as carbonyl moieties. Thus, these composite polymers are not useful with PTFE grafts.

Fluoroscopically visible medical device are known which include detectable coatings. U.S. Pat. No. 4,990,138 discloses an everting balloon catheter that is made radiopaque by bonding a polymeric material doped with a major amount of radiopaque metals onto a distal end portion a catheter body. The coating allows the distal end to be visible for use in guiding placement of the catheter body.

U.S. Pat. No. 6,048,362 discloses a radiopaque filler compound added to an elastic polymer. The polymer is then coated onto a metal frame to form a stent/graft device. In preferred embodiments, the radiopaque material contains barium, bismuth, or tungsten, and the polymer is treated with a porous coating to improve bio-compatibility. The result is a fluoroscopically visible stent/graft device.

Published Application No. WO 01/49340 to Pacetti and Mroz discloses a stent having enhanced radiopacity due to particles of radiopaque material contained within a binder that is used as a coating for the stent. This invention is limited to use on stents.

It is also known to coat the interior of an implantable device with radiopaque metals such as gold, platinum and tantalum by sputtering, evaporation or electroplating processes. It is a requirement of these coatings that they have good adhesion and conform to the medical device during deformation. Unfortunately, these coatings are susceptible to degradation over time. Cracking, flaking, and delamination can be a problem with this approach. When part of the coating separates from the substrate, there is a risk of causing turbulence in the blood flow and resultant thrombogenesis. Pieces may also create a risk of embolism in downstream vasculature.

While the prior art discloses various compositions and methods for rendering an implantable medical device radiopaque, there has yet to be developed an implantable medical device that is biocompatible, radiopaque, and does not lose effectiveness with time or risk injury to a patient. Thus, there is a present need for a radiopaque implantable medical device that is safe, biocompatible and biostable over time.

SUMMARY OF THE INVENTION

The present invention provides a radiopaque medical prosthesis that overcomes the disadvantages of the prior art. The prosthesis fulfills all the mechanical and structural requirements attendant to its function. In addition, the prosthesis is fluoroscopically visible without requiring a radiopaque material be provided separate from the prosthesis itself.

The advantages of the present invention are achieved by providing a radiopaque compound admixed with PTFE to form an integrally formed biocompatible implantable prosthesis. The integrity of the prosthesis is maintained by choosing appropriate relative amounts of the radiopaque material with respect to the prosthesis material.

The present invention provides a radiopaque implantable prosthesis including a polymeric prosthesis made from ePTFE having a node and fibril structure and a radiopaque filler, which is integral with at least a portion of the node and fibril structure of the prosthesis.

In an advantageous aspect, the present invention provides a radiopaque vascular graft, including a vascular graft formed from ePTFE having a node and fibril structure, and a radiopaque filler integral with at least a portion of the node and fibril structure of the graft. The filler is desirably a plurality of gold particles, although other materials are useful.

The present invention also provides a method of making a radiopaque implantable polymeric prosthesis made from PTFE and a radiopaque filler integral with a node and fibril structure of the prosthesis. The method includes the steps of admixing PTFE particles, a lubricant, and a radiopaque filler to form a mixture; pre-forming the mixture under pressure into a cylindrical billet; extruding the billet into an extrudate having a predetermined shape; expanding and/or stretching the extrudate to form an expanded radiopaque prosthesis wherein the radiopaque filler is integral with the node and fibril structure of the PTFE; and sintering the extruded radiopaque prosthesis to form a sintered radiopaque prosthesis. Desirably, the radiopaque filler is uniformly distributed throughout the prosthesis. A rinsing step may be performed to remove residual radiopaque filler from the cooled radiopaque prosthesis.

In a desirable aspect, the present invention provides a medical device in the form of a prosthesis formed into a tube or sheet to serve as a graft or patch, respectively. The prosthesis in the form of a graft may be used alone or in combination with a stent. Additionally, the graft/stent combination may be formed as a graft covered stent, a stent covered graft, a stent arranged between two grafts, a laminated graft and stent combination, and the like.

With the foregoing and additional features in mind, this invention will now be described in more detail, and other benefits and advantages thereof will be apparent from the following detailed description when taken in conjunction with the accompanying drawings.

DETAILED DESCRIPTION OF THE DRAWINGS

DETAILED DESCRIPTION OF THE INVENTION

An implantable prosthesis made in accord with the present invention provides the distinct advantage of permitting fluoroscopic viewing of the prosthesis at any time. This advantage allows non-invasive diagnostic evaluation of prosthesis performance including location, patency, and compliance of the graft, the anastomosis of the graft to the patient's body organ tubing, and the presence or absence of conditions such as holes, kink failures, bursts, aneurysm, and the like. The prosthesis of the present invention remains radiopaque throughout the life of the prosthesis without losing radiopacity. Advantageously, the radiopacity of the prosthesis of the present invention is opaque enough to enable detection yet not so opaque as to interfere with other non-invasive diagnostic techniques such as angiography.

Figure 1:
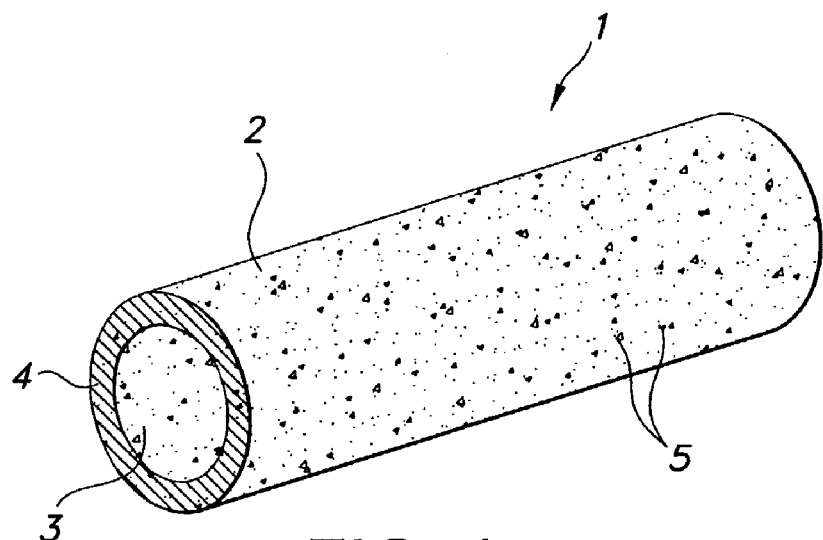
FIG. 1 is a perspective view of an implantable prosthesis according to the invention.

Referring now to FIG. 1, an embodiment of the present invention in the form of an ePTFE vascular graft, is shown. The graft 1 is an elongate tube having an exterior surface 2, an interior surface 3 and a cross sectional thickness 4. A radiopaque material 5 is uniformly interspersed throughout the graft 1. This uniform distribution of radiopaque material 5 allows a practitioner to view the graft 1 fluoroscopically throughout its entire length.

Figure 2B:
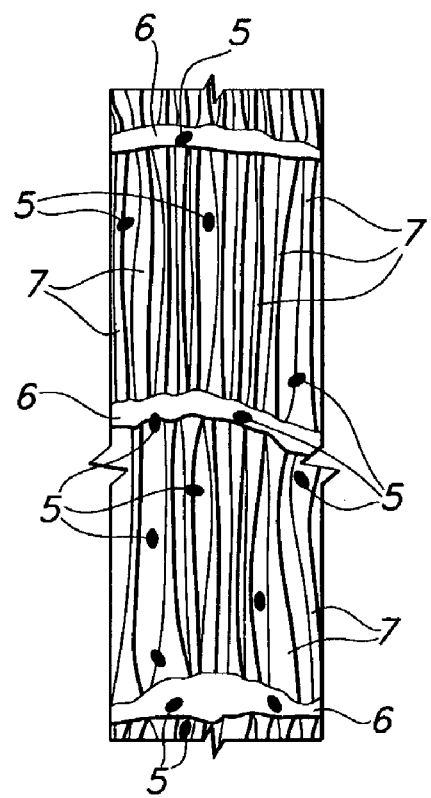
FIG. 2B is an exaggerated detail view of the nodes and fibrils of an implantable prosthesis according to the present invention made with ePTFE and having radiolabeled material therein.
Figure 2A:
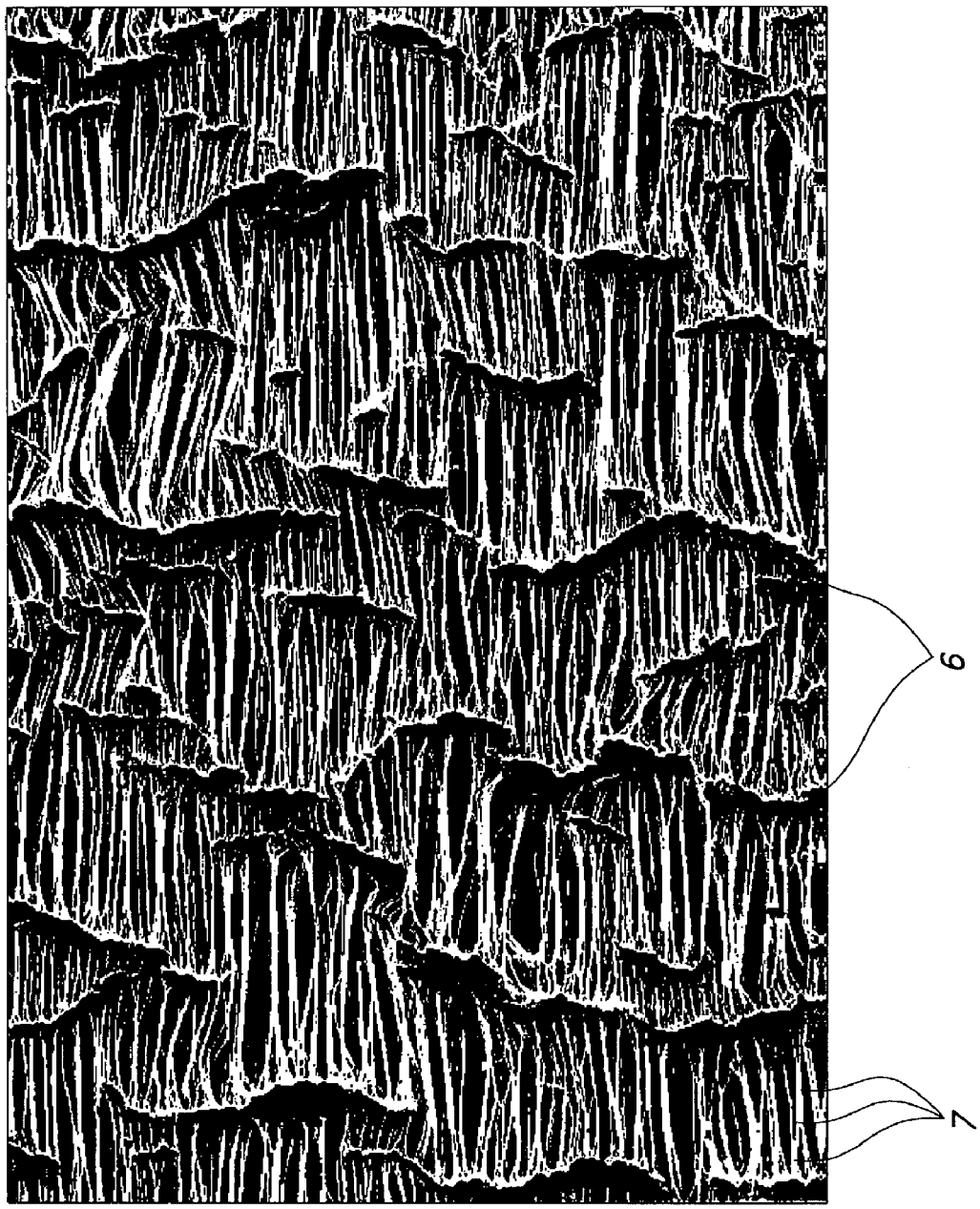
FIG. 2A is a photomicrograph showing a longitudinally expanded PTFE structure of the prior art.

Referring now to FIGS. 2A and 2B, an enlarged view of the microstructure of ePTFE is shown. In FIG. 2A, the prior art is shown in which nodes 6 are connected to one another by bundles of fibrils 7. In FIG. 2B, a greatly enlarged and exaggerated detail view of the internal structure of ePTFE with the radiopaque filler material or particles integral with the nodes and fibrils is shown. The node 6 and fibril 7 structure is seen having radiopaque material 5 both fully integral or partially integral with the nodes 6 themselves as well as fully integral or partially integral with the fibrils 7. By fully integral with the nodes and/or fibrils is meant that the entire particle is surrounded by PTFE. By partially integral with the nodes and/or fibrils is meant that part of the particle is surrounded by PTFE while part of the particle is in the porous spaces of the PTFE. Additionally, some radiopaque material ultimately ends up interspersed among the fibrils 7. This material is still integral with the PTFE if it remains embedded or entrapped within the fibril bundles after the rinsing step of the process.

Although not intending to be limited to such interpretation, it is believed this integration of radiopaque material is made possible due to the expansion process of the PTFE extrudate which forms the ePTFE node and fibril structure. It is thus possible for the radiopaque material to be generally uniformly distributed throughout the entire prosthesis in both the cross sectional thickness as well as its length. Furthermore, it is possible for the radiopaque material to remain substantially permanently within the ePTFE structure once implanted into a patient. In one advantageous aspect of the invention, the majority of the radiopaque material is at least partially integrated within the nodes and fibrils of the ePTFE structure.

One method for manufacturing porous PTFE tubing generally, is described, for example, in U.S. Pat. No. 3,953,566, U.S. Pat. No. 3,962,153, and U.S. Pat. No. 4,973,609, the entireties of which are herein incorporated by reference. Generally, a PTFE tube may be formed in four steps including preparation of a PTFE paste, extrusion of a tube, expansion of the tube, and sintering of the tube. When forming tubular structures PTFE paste is either formed into a billet under pressure and passed through a tubular extrusion dye or coated onto a mandrel to form a tubular extrudate. Next, the wet extrudate is dried to evaporate the lubricant at either room temperature or temperatures near the lubricant's dry point. After the PTFE resin or paste is formed and dried, it is expanded and may also be stretched while being formed into the desired tube shape. Stretching refers to elongation of formed resin while expansion refers to enlargement of the formed resin perpendicularly to its longitudinal axis. The stretching/expansion step occurs at a temperature less than 327° C., typically in the range of 250-326° C. by an expansion rate of at least two to one (2:1). Finally, the tubular extrudate is sintered by heating it to a temperature of about 350-370° C. This results in an amorphous locking of the polymer. The tubular extrudate may then be cut to size.

Similarly, a method for manufacturing porous ePTFE sheets is described in U.S. Pat. No. 5,476,589, the entirety of which is herein incorporated by reference. Generally, formation of sheets is similar to that of forming tubes. However, rather than being only expanded, the extrudate is stretched to form the desired ribbon or sheet. The sintered extrudate may then be cut to size as tapes, patches, or the like.

The radiopaque ePTFE according to the invention may be prepared as follows. A PTFE paste dispersion is made by admixing a fine, virgin PTFE powder such as F-104, F-103, Virgin PTFE Fine Powder (Dakin America, Orangeburg, N.Y.) with a liquid lubricant such as odorless mineral spirits or naphtha, i.e., Isopar® (Exxon Chemical Co., Houston, Tex.), and radiopaque particles such as gold powder (Alfa Aesar, Ward Hill, Mass.) to form a PTFE paste so as to evenly distribute the radiopaque powder among the PTFE into a paste having the desired consistency. The mixture is then pre-formed into a cylindrical billet under pressure, for example from about 300 psi to about 600 psi. The pre-formed billet is then extruded to a rod or tubular extrudate. The extrudate is then expanded and/or stretched and formed into a predetermined shape such as a tube or sheet, at an elevated temperature not exceeding about 327° C. The extrudate is then sintered at a temperature in excess of about 327° C. to crystallize the extruded structure. The length of the sintering step may be less than that for conventional ePTFE sintering, due to the heat sink aspects of the gold particles in the material. One having ordinary skill will be able to adjust the time for sintering in relation to the amount of radiopaque material in the extrudate. The extrudite is rinsed so as to remove any residual radiopaque particles that have not been trapped in the ePTFE prior to implantation. As a final step, the extrudite may be cut to the desired end use shape.

In a desirable aspect, the radiopaque filler is substantially uniformly distributed throughout the radiopaque ePTFE. To this end, thorough mixing of the PTFE paste dispersion is important to assist in uniformly distributing the radiopaque filler throughout the paste. This is also important from a cost standpoint, as the radiopaque filler can be expensive. Thorough mixing of the material will aid in minimizing loss of the radiopaque filler in the rinsing stage of the process. In addition, the pressure used to pre-form the billet and then to form the prosthesis will assist in providing a uniform distribution of radiopaque particles throughout the prosthesis. Specifically, extruding or working the material under pressure also serves to uniformly distribute the radiopaque filler.

In an advantageous aspect, a physiologically or pharmacologically active agent may be coated or otherwise incorporated into a prosthesis made with the radiopaque ePTFE according to the invention so as to allow for timed released delivery to a patient after implantation. Any drug or biotherapeutic agent may be coated onto a surface or incorporated into the prosthesis. Examples of suitable drugs or biotherapeutic agents may include, without limitation, thrombo-resistant agents, antibiotic agents, anti-tumor agents, cell cycle regulating agents, their homologs, derivatives, fragments, pharmaceutical salts, and combinations thereof.

Useful thrombo-resistant agents may include, for example, heparin, heparin sulfate, hirudin, chondroitin sulfate, dermatan sulfate, keratin sulfate, lytic agents, including urokinase and streptokinase, their homologs, analogs, fragments, derivatives and pharmaceutical salts thereof.

Useful antibiotics may include, for example, penicillins, cephalosporins, vancomycins, aminoglycosides, quinolones, polymyxins, erythromycins, tetracyclines, chloramphenicols, clindamycins, linomycins, sulfonamides, their homologs, analogs, fragments, derivatives, pharmaceutical salts and mixtures thereof.

Useful anti-tumor agents may include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and mixtures thereof.

Useful anti-viral agents may include, for example, amantadines, rimantadines, ribavirins, idoxuridines, vidarabines, trifluridines, acyclovirs, ganciclovirs, zidovudines, foscarnets, interferons, their homologs, analogs, fragments, derivatives, pharmaceutical salts and mixtures thereof The agent may be provided in any of a variety of methods. For example, it is possible to form the ePTFE prosthesis with monomers including functional groups to which the agents will bind. The prosthesis can be dip coated with a mixture of a drug in an appropriate buffer. After allowing the drug to react with the functional groups, the graft may be dried. See the method as taught in U.S. Pat. No. 6,358,557, for example. Alternatively, it is also possible to use the porous nature of the ePTFE material to hold therapeutic agents therein. The therapeutic agent may be added to the prosthesis by addition of a therapeutic drug solution under pressure.

The particle size of the radiopaque filler will desirably be from about 0.05 to about 2 microns in diameter. More desirably, the particle size will be within the range of 0.05 microns to about 0.5 microns in diameter, even more desirably from about 0.05 microns to about 0.1 microns in diameter. It is desirable for a majority of the particles to remain at least partially integrated in the nodes and/or in the fibrils. The particles will also be useful if integrated by being trapped among fibril bundles so as to avoid release upon rinsing or implantation. When the particles are trapped among fibril bundles, it may be possible for some of the particles to escape the bundle and reach the bloodstream. In this case, the small size of the particles is advantageous, as it will serve to avoid embolisms, which are typically associated with larger particles or masses in the bloodstream. Additionally, the chance of radiopaque filler being released into the bloodstream is limited due to normal tissue growth of intima that occurs after implantation. The cells serve to secure the place of the radiopaque filler in the structure. It is further desirable for the filler particles to be substantially uniform in size.

Suitable compounds for the radiopaque material include metals such as platinum, stainless steel, titanium, silver, tantalum, barium, bismuth, iridium, tungsten, rhenium, osmium, iridium, or palladium and biocompatible oxides thereof. Desirably, the material is gold, titanium, or silver and biocompatible oxides thereof. More desirably, the material is gold having a purity of at least 99%. As used herein a material is biocompatible if it does not significantly compromise the function of the host organism. The radiopaque materials may be used alone or in combination. The radiopaque material may be coated with a biocompatible material such as a resin.

The concentration of the radiopaque filler material will vary depending on the application. Generally, the concentration should be high enough to be clearly detectable fluorometrically yet be low enough to maintain the structural integrity of the prosthesis and to avoid interfering with other radiopaque diagnostics such as angiography and the like. Generally, the radiopaque material is from about 5% to about 30% by weight of the prosthesis. Desirably, the radiopaque material is from about 10% to about 25% by weight of the prosthesis. More desirably, the radiopaque material is about 20% by weight of the prosthesis. Although desired concentrations of radiopaque material have been delineated, other concentrations outside of these ranges may be suitable, depending on the ultimate use of the radiopaque ePTFE in a prosthesis. These ranges also fall within the scope of the invention.

The radiopaque ePTFE can be used in any medical application in which ePTFE prostheses are used. For example, the radiopaque ePTFE can be used in grafts, stents, surgical felts, or the like. Grafts are tubular medical devices used to repair or replace damaged vessels. They may be formed of a variety of materials. In the present invention, ePTFE is used. A stent provides structural support to hold a damaged vessel open. Stents are usually used in combination with grafts in which the graft is a liner, a cover, laminated, adhered, sewn or otherwise attached to the stent. It is to be understood that the prosthesis according to the invention may be in the form of a structurally self-supporting graft. Specifically, it can be used as a graft without requiring a stent for support. Surgical felts are used as patches to repair non-tubular defects. The implantable prosthesis may be chosen from a wide variety of prostheses including but not limited to catheters, balloons, grafts, graft/stent combinations, surgical felts, and the like.

In one advantageous aspect of the invention, the prosthesis is an ePTFE graft with radiopaque gold particles integrated therein. However, any implantable medical device that may be formed of ePTFE can be rendered radiopaque in accord with the invention. For example, in one embodiment, a conventional ePTFE graft can be bonded along a portion of the graft with a radiopaque ePTFE ribbon made according to the invention.

Figure 3:
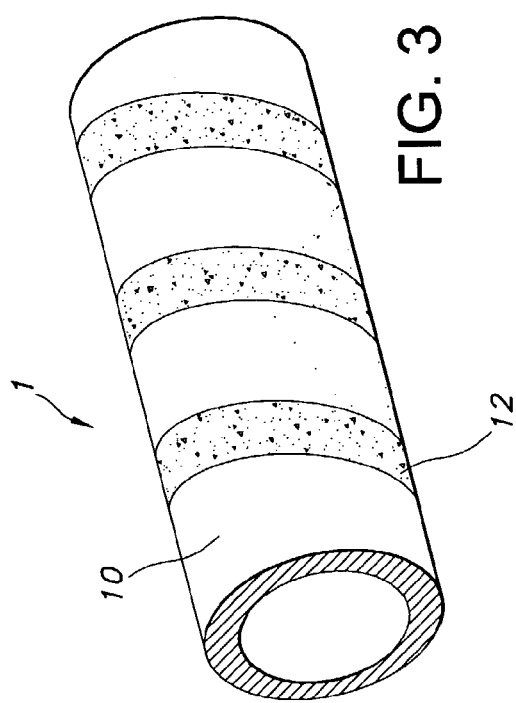
FIG. 3 is a perspective view of a prosthesis made with a ribbon of radiopaque ePTFE according to the invention wrapped around a conventional graft.

Referring now to FIG. 3, an embodiment of the present invention is shown in which a conventional graft 10 is rendered radiopaque by having a ribbon 12 made with radiopaque ePTFE according to the invention wrapped around it. The ribbon 12 includes the radiopaque material 5 as previously described. It is also possible for a conventional graft to be rendered radiopaque by being bonded with individual rings of the radiopaque ePTFE either intermittently along the length of the graft or only at the ends thereof. Bonding of the ePTFE to the conventional graft may be accomplished by methods that are known in the art such as via an adhesive or heat. It is also possible to position a radiopaque ePTFE portion onto an otherwise conventional graft with the aid of a stent to hold the radiopaque portion in place or to use the stent in combination with known bonding techniques.

The opacity of the radiopaque ePTFE may be varied depending on the application. In applications involving tubular grafts, for example, certain diagnostic tests are focused on identifying proper placement of the graft. In this case, the graft may be made with substantially radiopaque ePTFE, or it may be bonded intermittently along the length of the graft, for example with a ribbon or series of rings of substantially radiopaque ePTFE according to the invention. The high degree of opacity will enable a practitioner to identify the exact location of the graft implant.

In other diagnostic tests involving grafts, such as fluoroscopy tests designed to evaluate blood flow through a graft, it may be necessary to see the entire length of the graft while still being able to view a dye flowing therethrough. In this case, the radiopacity will be partial or "radiotranslucent" to allow both viewing of the structural integrity of the entire graft and detection of the dye indicating the ability of blood to flow through the graft.

Regulation of the degree of opacity of the radiopaque ePTFE may be accomplished by varying the amount of radiopaque filler in the PTFE paste. Opacity will be increased by increasing the relative amount of filler to PTFE in the paste and decreased by decreasing the relative amount of filler to PTFE in the paste. Furthermore, regulation of the degree of opacity may be accomplished by varying one or more of the process parameters described above. For example, for a given concentration of radiopaque filler added to the PTFE paste, a lesser percent of expansion, for example 500%, will result in a greater concentration of radiopaque material and increased radiopacity. This is most suitable in applications involving a prosthesis having a thicker cross-section. To reduce the degree of opacity, a greater percent of expansion, for example 2000-3000%, will result in less opacity or a radiotranslucent ePTFE. It is also possible to increase the rate of expansion, and/or pulse the expansion to occur in abrupt cycles so as to increase the node to fibril ratio of the resulting ePTFE. This rate and kind of expansion will similarly result in an increase in opacity of the ePTFE product thus formed. Other variations in the process will be apparent to those of skill in the art, and are envisioned as within the scope of the invention.

Figure 4:
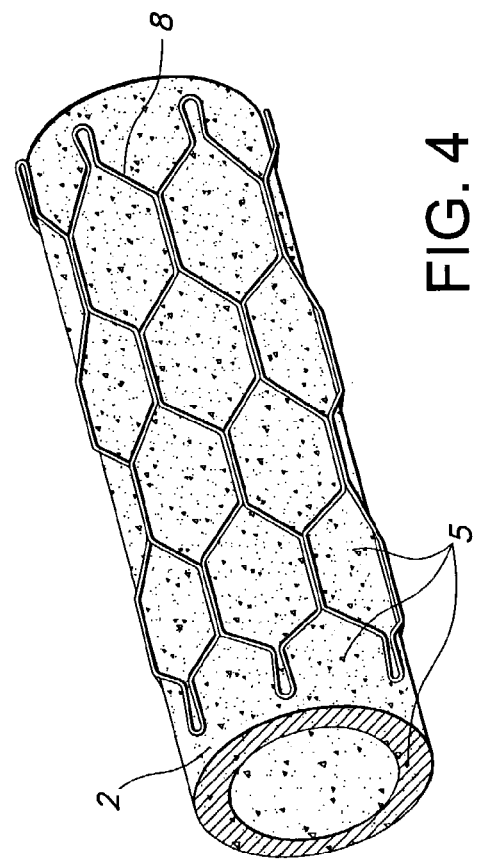
FIG. 4 is a perspective view of a stent/graft combination prosthesis.

Referring now to FIG. 4, a stent/graft combination prosthesis is shown. In this embodiment, the graft 1 is covered with the stent 8. The radiopaque material 5 is uniformly distributed throughout the graft 1 rendering the combination device detectable by radiological means. Variations of this design are also within the scope of the invention. Therefore, it is also possible for the stent to be sandwiched between two grafts, or for a stent to be covered by a conventional graft that is further wrapped in a ribbon of radiopaque ePTFE, or combinations thereof. There are no particular limitations to the design of prostheses using the radiopaque ePTFE of the present invention, so long as the resulting prosthesis is radiopaque.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention, and it is intended to claim all such changes and modifications to fall within the scope of the invention.

I claim:

1. A radiopaque implantable stent-graft, comprising:
a polymeric prosthesis having inner and outer surfaces and an extruded tubular shape, said polymeric prosthesis being made from ePTFE having a node and fibril structure with nodes and fibrils; and
a radiopaque filler fully integral with said nodes and fibrils, wherein said radiopaque filler is present in amounts sufficient to be fluorometrically detectable, avoid interfering with angiography procedures and still maintain structural integrity of the polymeric prosthesis, said amounts ranging from about 5% to about 20% by weight, said radiopaque filler being distributed therein to form radiotranslucent portions of said polymeric prosthesis,
wherein said polymeric prosthesis is free of said radiopaque filler on the inner and outer surfaces; and
a stent disposed over the extruded tubular shape.

2. The radiopaque implantable stent-graft according to claim 1, wherein said radiopaque filler is uniformly distributed in said polymeric prosthesis.

3. The radiopaque implantable stent-graft according to claim 1, wherein said radiopaque filler is particles, said particles have an average diameter of from about 0.05 microns to about 2 microns.

4. The radiopaque implantable stent-graft according to claim 1, wherein said radiopaque filler is in the form of particles, said particles have an average diameter of from about 0.05 microns to about 0.5 microns.

5. The radiopaque implantable stent-graft according to claim 4, wherein said particles have an average diameter of from about 0.05 microns to about 0.1 microns.

6. The radiopaque implantable stent-graft according to claim 1, wherein said radiopaque filler is a material formed with particles comprising at least one member selected from the group consisting of platinum, stainless steel, silver, barium, bismuth, iridium, rhenium, osmium, palladium, gold, and oxides thereof.

7. The radiopaque implantable stent-graft according to claim 1, wherein a portion of the polymeric prosthesis that is rendered radiopaque has a uniform characteristic with said radiopaque filler being evenly distributed throughout said portion.

8. The radiopaque implantable stent-graft according to claim 1, wherein the stent-graft is bound by edges provided at distal ends of said extruded tubular shape having a structural integrity to be implantable into a patient's body.

9. The radiopaque implantable stent-graft of claim 1 wherein said radiopaque filler is a plurality of radiopaque particles.

* * * * *